United States Patent
Canli et al.

(10) Patent No.: US 10,258,251 B2
(45) Date of Patent: Apr. 16, 2019

(54) BREAST CANCER IMAGING DEVICE THROUGH MICROWAVE SURFACE IMPEDANCE

(71) Applicant: MITOS MEDIKAL TEKNOLOJILER SANAYI VE TICARET ANONIM SIRKETI, Istanbul (TR)

(72) Inventors: Guray Ali Canli, Istanbul (TR); Ibrahim Akduman, Istanbul (TR); Mehmet Cayoren, Istanbul (TR); Ali Yapar, Istanbul (TR); Hulya Sahinturk, Istanbul (TR)

(73) Assignee: MITOS MEDIKAL TEKNOLOJILER SANAYI VE TICARET ANONIM SIRKETI, Istanbul (TR)

( * ) Notice: Subject to any disclaimer, the term of this patent is extended or adjusted under 35 U.S.C. 154(b) by 763 days.

(21) Appl. No.: 14/768,321

(22) PCT Filed: Feb. 12, 2014

(86) PCT No.: PCT/TR2014/000034
§ 371 (c)(1),
(2) Date: Aug. 17, 2015

(87) PCT Pub. No.: WO2014/126540
PCT Pub. Date: Aug. 21, 2014

(65) Prior Publication Data
US 2016/0106334 A1    Apr. 21, 2016

(30) Foreign Application Priority Data

Feb. 15, 2013 (TR) ............................... a 2013 01886
Nov. 15, 2013 (TR) ............................... a 2013 13275

(51) Int. Cl.
*A61B 5/05* (2006.01)
*A61B 5/00* (2006.01)
(Continued)

(52) U.S. Cl.
CPC .......... *A61B 5/0507* (2013.01); *A61B 5/0073* (2013.01); *A61B 5/0536* (2013.01);
(Continued)

(58) Field of Classification Search
CPC ..... A61B 5/708; A61B 5/7264; A61B 5/0507; A61B 5/0536; A61B 5/4312; A61B 5/0073; A61B 5/1079
See application file for complete search history.

(56) References Cited

U.S. PATENT DOCUMENTS 4,641,659 A * 2/1987 Sepponen ................ A61B 5/05
600/430
8,323,201 B2 * 12/2012 Towfiq ................ A61B 8/0825
600/437
(Continued)

FOREIGN PATENT DOCUMENTS

WO     2011163359 A2    12/2011

OTHER PUBLICATIONS

International Search Report for corresponding International Application No. PCT/TR2014/000034.
(Continued)

*Primary Examiner* — Bo Joseph Peng
(74) *Attorney, Agent, or Firm* — Egbert, McDaniel & Swartz, PLLC

(57) ABSTRACT

A breast cancer imaging device with microwave surface impedance is a device which is used for imaging tumors in breast tissue using harmless electromagnetic waves in microwave band. It performs this function by using harmless electromagnetic waves without using X-ray. Thus, it can be (Continued)

Figure 1:
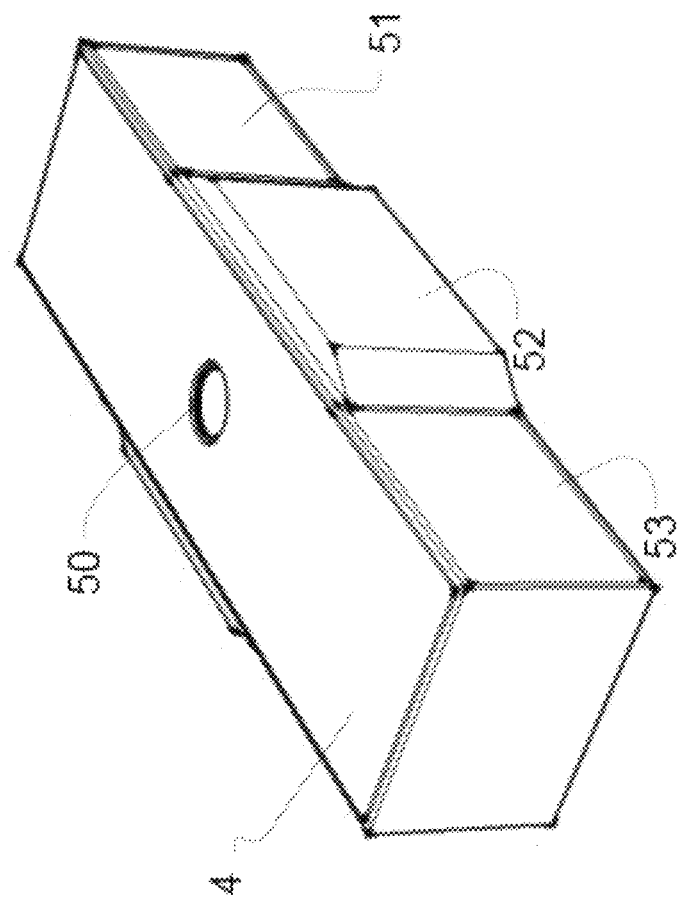

performed in desired frequency, as many times as desired. Since compressing the breasts is no longer required, it is not a painful imaging process for the patient; moreover, it does not fail to detect the tumors that are close to the rib cage.

9 Claims, 9 Drawing Sheets

(51) Int. Cl.
*A61B 5/053* (2006.01)
*A61B 5/107* (2006.01)
(52) U.S. Cl.
CPC ............ *A61B 5/4312* (2013.01); *A61B 5/708* (2013.01); *A61B 5/7264* (2013.01); *A61B 5/1079* (2013.01)

(56) References Cited

U.S. PATENT DOCUMENTS

| 2004/0077943 | A1 | 4/2004 | Meaney et al. |
| 2010/0113921 | A1 | 5/2010 | Fear et al. |
| 2010/0121318 | A1* | 5/2010 | Hancock ................ A61B 18/18 606/33 |

OTHER PUBLICATIONS

Paul M Meaney et al: "Microwave tomography in the context of complex breast cancer imaging", 2010 Annual International Conference of the IEEE Engineering in Medicine Andbiology Society : (EMBC 2010) ; Buenosaires, Argentina, Aug. 31-Sep. 4, 2010, IEEE, Piscataway, NJ, USA,Aug. 31, 2010 (Aug. 31, 2010), pp. 3398-3401.

Pallone Matthew J et al: "Surface scanning through a cylindrical tank of coupling fluid for clinical microwave breast imaging exams", Medical Physics, AIP, Melville, NY, US, vol. 39, No. 6, May 14, 2012 (May 14, 2012), pp. 3102-3111.

Padhi Shantanu et al: "A PC-controlled microwave tomographic scanner for breast imaging", Review of Scientific Instruments, AIP, Melville, NY, US, vol. 82, No. 1, Jan. 21, 2011 (Jan. 21, 2011), pp. 14702-14702.

Grzegorczyk T M et al: "Fast 3-D Tomographic Microwave Imaging for Breast Cancer Detection", IEEE Transactions on Medical Imaging, IEEE Service Center, Piscataway, NJ, US, vol. 31, No. 8, Jul. 27, 2012 (Jul. 27, 2012), pp. 1584-1592.

Li Dun et al: "Comparisons of three alternative breast modalities in a common phantom imaging experiment", Medical Physics, AIP, Melville, NY, US, vol. 30, No. 8, Jul. 25, 2003 (Jul. 25, 2003), pp. 2194-2205.

Rabah Al Abdi et al: "Optomechanical imaging system for breast cancer detection", Journal of the Optical Society of America. A, Optics, image science, and vision, Nov. 11, 2011 (Nov. 11, 2011), pp. 2473; Retrieved from the Internet: URL:http://www.ncbi.nlm.nih.gov/pubmed/221 93261 [retrieved on May 26, 2014] p. 2475, col. 1, line 1—p. 2476.

* cited by examiner

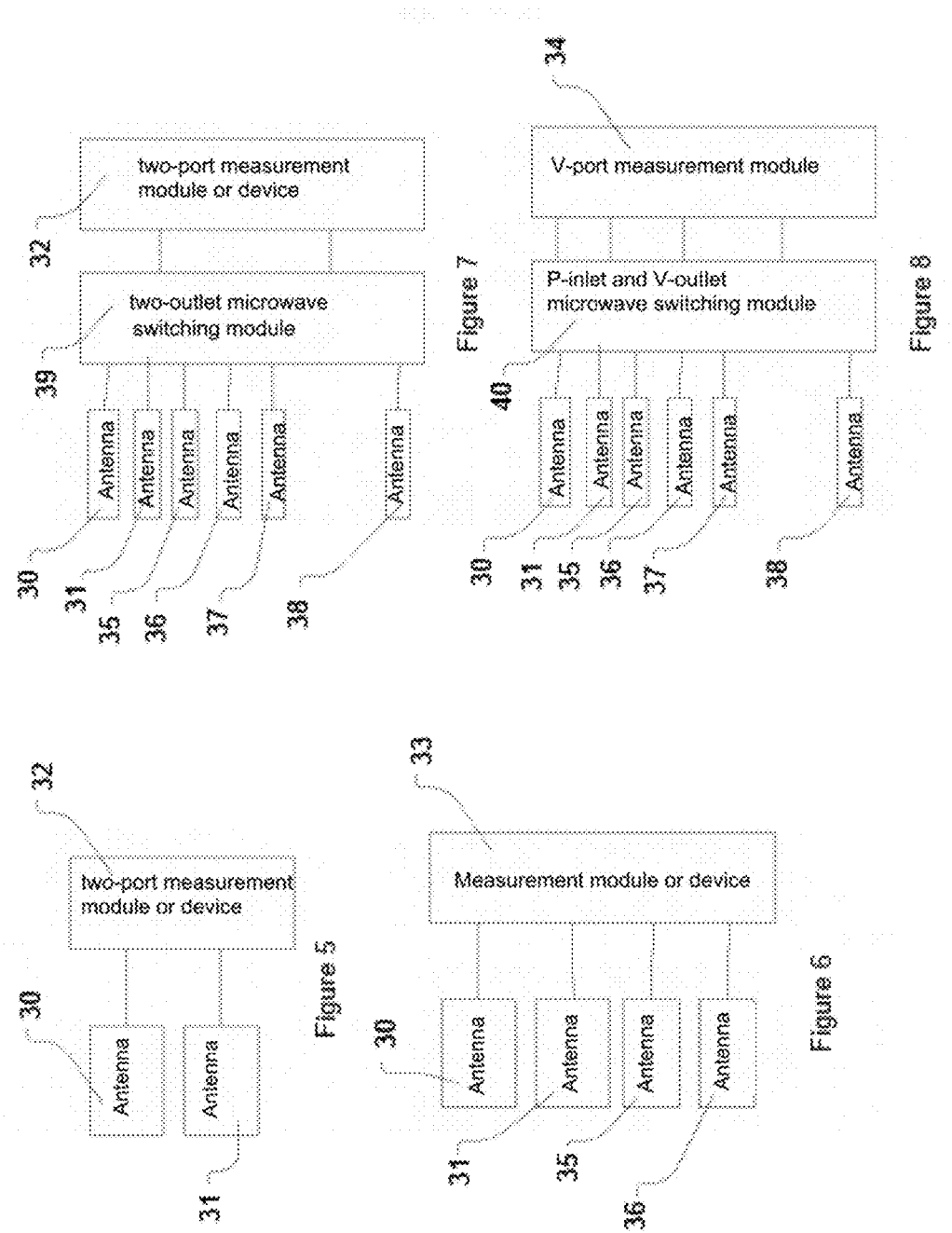

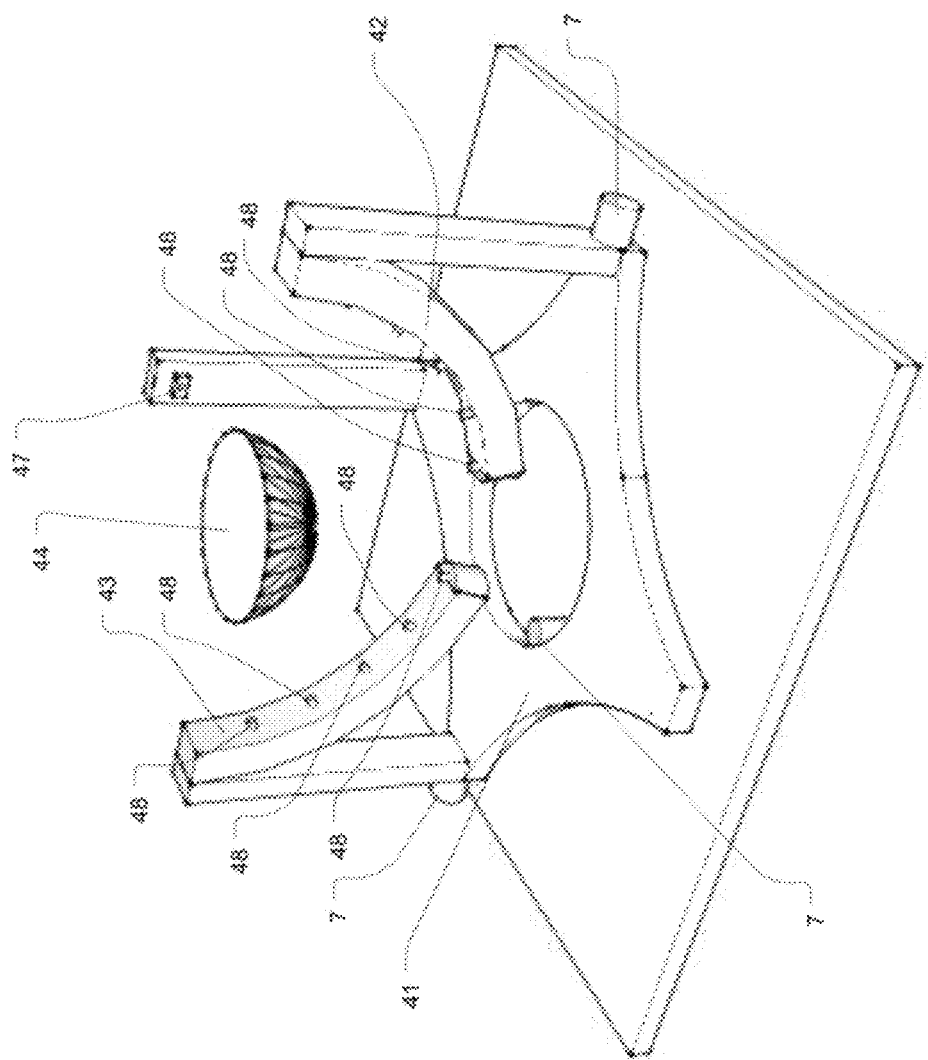

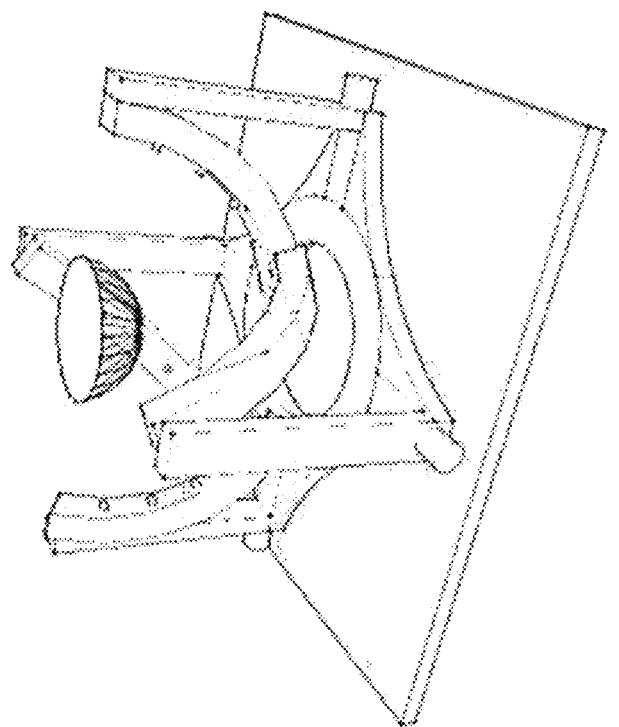
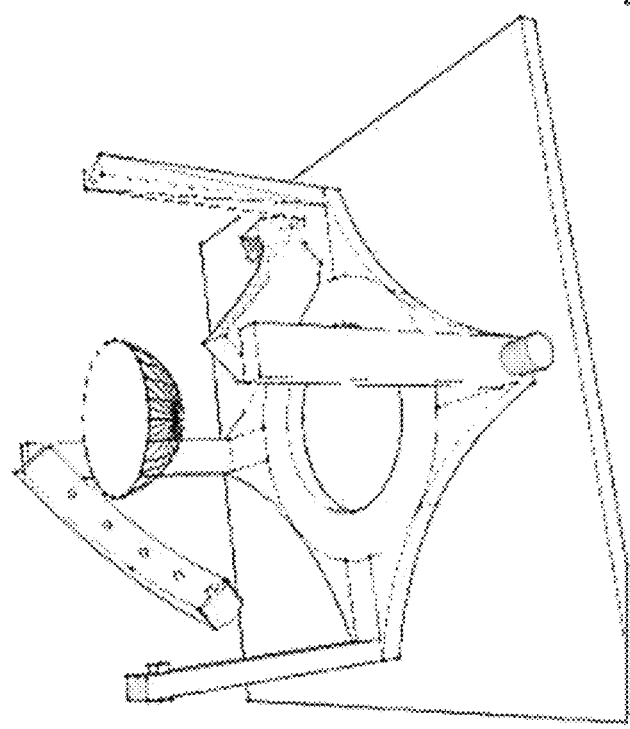
Figure 12

BREAST CANCER IMAGING DEVICE THROUGH MICROWAVE SURFACE IMPEDANCE

TECHNICAL FIELD

The invention relates to breast cancer imaging device through microwave surface impedance.

STATE OF THE ART

Breast cancer is one of the most threatening diseases affecting women and the most significant way to fight against breast cancer is early diagnosis, when cancerous tissues are in the phase of formation. Common practice is to use X-ray tomography for breast tumor diagnosis X-ray tomography (mammography) is an industrial standard in breast tumor diagnosis. However, X-ray tomography has some known disadvantages. These are as follows:

1. Since X-ray is an ionizing radiation, it may as well cause cancer itself. Therefore, frequent application of mammography is a risk itself.
2. Mammography requires com60
3. pressing the breast for imaging. Therefore, it is a painful process.
4. Mammography cannot be performed before breast tissue development is completed. This, in turn, happens at the end of the breastfeeding period, generally after the age of 40.
5. Since imaging is performed after the breast is compressed physically, the tumors that are close to the rib cage cannot be detected.

Although mammography is the most common standard in this field, it can only detect tumors of certain size, with a certain error rate. The tumor size that is detected with high probability is 10 mm. The tumors smaller than 8 mm, however, may not be detected. Despite these disadvantages, there is no other method to replace mammography.

Today, as an alternative to mammography studies using electromagnetic waves operating in microwave band are carried out. Some of those approaches use radar principle with pulsed wave. The device which is the subject of the invention differs from those studies in that it uses continuous wave. In addition, different approaches may be employed according to the structure of scanning system. For example, in some studies around the world, instead of mechanical scanning-system, scanning system with multiple fixed antennas are used as an alternative. The disadvantage resulting from the interactions among the antennas (there are systems where nearly a hundred antennas are used) is tried to be eliminated by filling the whole system with salty water. As is well known, salty water hardly transmits electromagnetic waves in microwave band. The device according to the invention makes measurements by mechanically positioning the antennas that are relatively fewer in numbers.

OBJECTIVE OF THE INVENTION

The breast cancer imaging device through microwave surface impedance, according to the invention, is a device which is used for imaging tumors in breast tissue using electromagnetic waves in microwave band. It performs this function by using harmless electromagnetic waves in any frequency in microwave band, without using X-ray. Thus, it can be performed as many times as desired. Since compressing the breasts is no longer required, it is not a painful process; moreover, it does not fail to detect the tumors that are close to the rib cage.

One of the objectives of the invention is to estimate surface impedance on breast surface by measuring the electric field due to the scattering of the electromagnetic waves excited by antennas moving mechanically on a hemispherical surface. The surface impedance is calculated by the use of reconstruction algorithm. Then the detection of breast tumors in a tomographic form is obtained by the analysis of the reconstructed surface impedance.

One of the objectives of the invention is to estimate surface impedance without tumor by means of the known methods in the art, to detect tumors much smaller in size with a higher rate by subtracting the surface impedance estimated with imaging algorithm software through the measurements performed by the device according to the invention.

One of the objectives of the invention is to decide whether tumor-like structures observed in the breast are malign or benign by classifying dielectric parameters of the tissues by using the imaging algorithm software.

Another objective of the invention is to measure the whole electric field of the breast in an accurate and sensitive manner in a short time, by electronically activating/deactivating the multiple wideband antennas located in the arms of a multi-axis/multi-arm electromechanical scanner operating hemispherically. During the movement of the arms the scattering parameters are measured for non-invasive detection of the tumor inside breast by using microwave and surface impedance methods. Non-invasive: means without touching or damaging. For instance biopsy is an invasive procedure. However, ultrasound is regarded as a non-invasive method. As another example, hemoglobin measurement with blood test is an invasive method, while hemoglobin measurement performed through light transmittance from fingertip is non-invasive.

One of the objectives of the invention is to measure the scattered electric field by means of the scattering parameters of electromagnetic waves and by means of a rotary axis mechanical scanning system with multiple arms operating in accordance with the algorithm, while using a plurality of measurement antennas and while activating them as receiver/transmitter in accordance with the desired algorithm via electronic ignition.

The structural and characteristic aspects and all advantages of the present invention will be more clearly understood by means of following figures and the detailed description written with reference to these figures. Therefore, while making an evaluation, these figures and the detailed description should be taken into account.

BRIEF DESCRIPTION OF THE FIGURES ALLOWING A BETTER UNDERSTANDING OF THE INVENTION

FIG. 1: The view showing all components of the breast cancer imaging device with microwave surface impedance.

Figure 2:
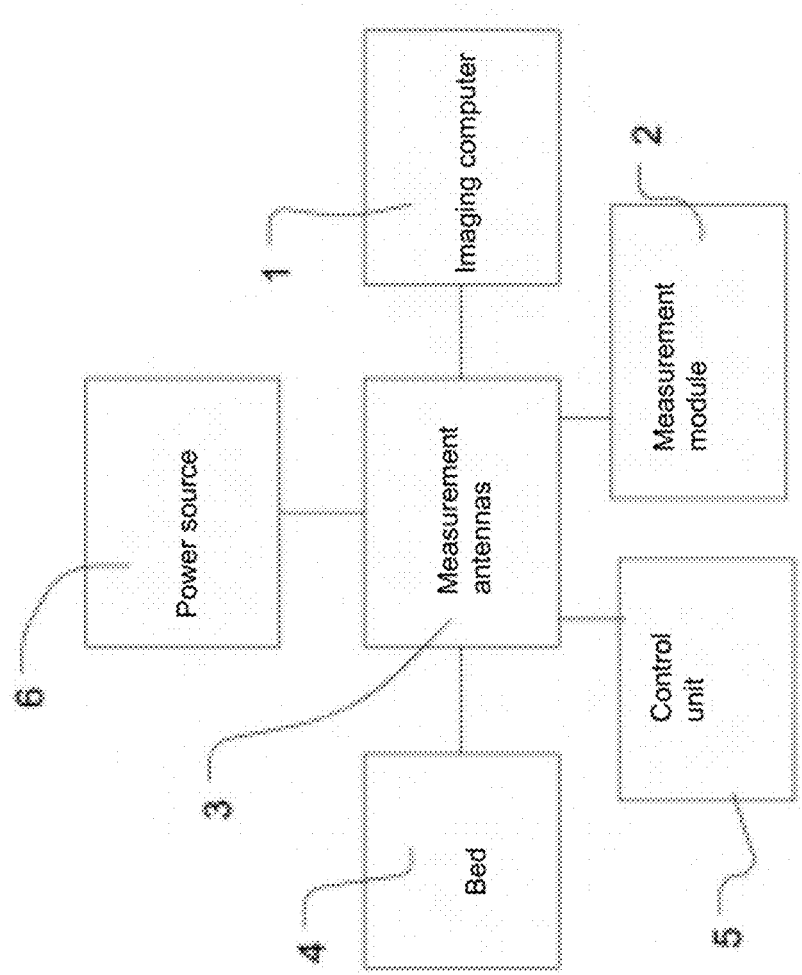

FIG. 2: The block diagram of the main components of the breast cancer imaging device with microwave surface impedance.

Figure 3:
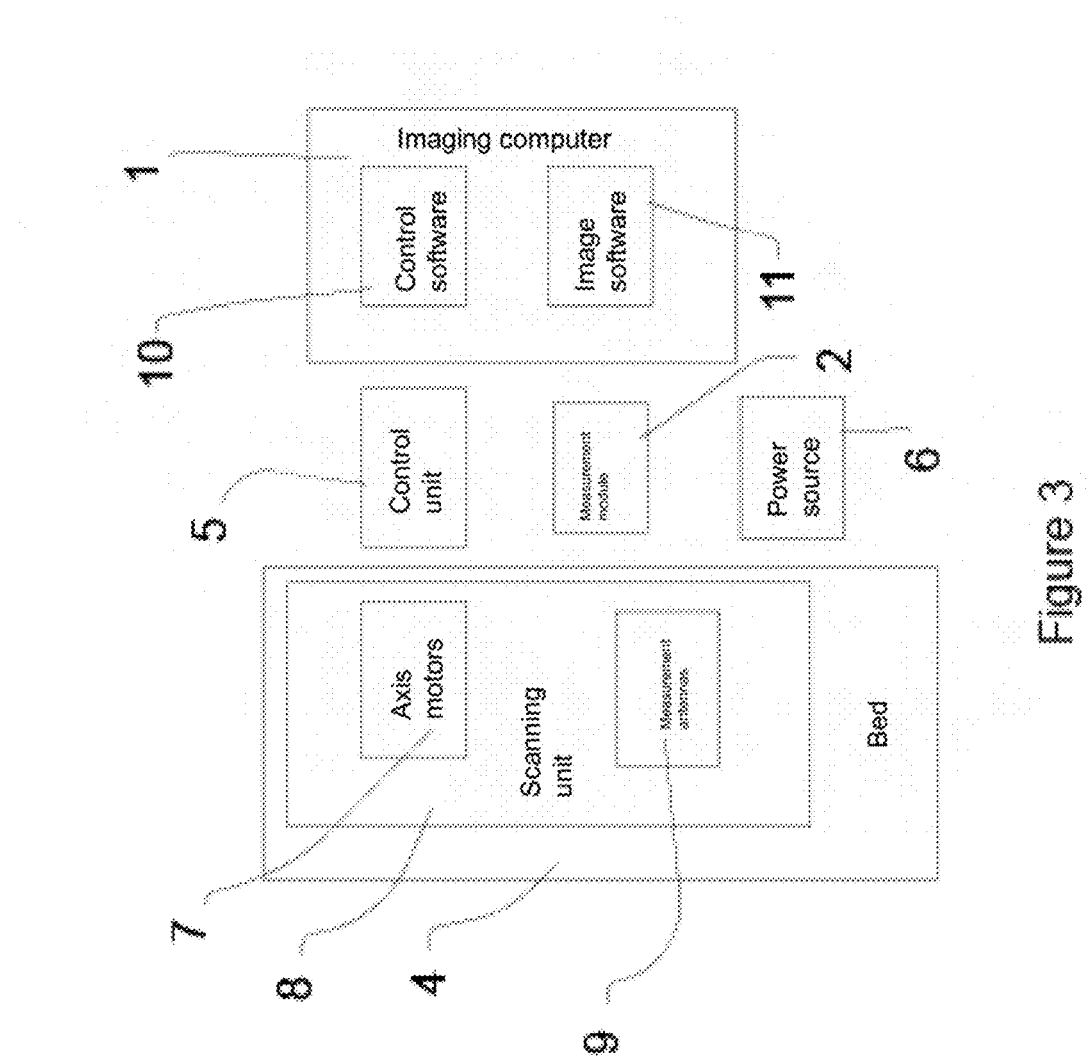

FIG. 3: The block diagram of the lower units of the breast cancer imaging device with microwave surface impedance.

Figure 4:
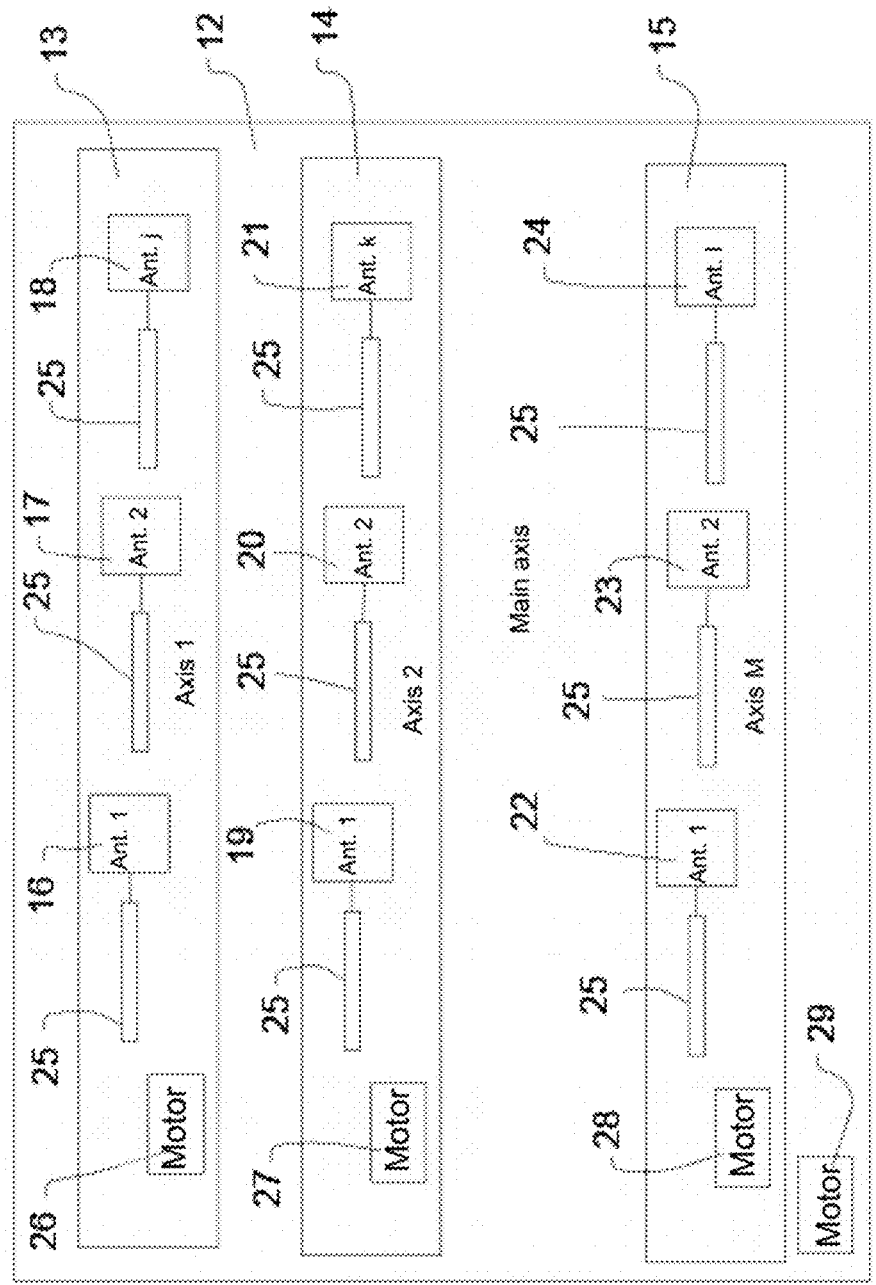

FIG. 4: The overall principle diagram of the scanning unit.

FIG. 5: The measurement principle diagram of the measurement module system with S parameter, 2 measurement antennas, and 2 ports FIG. 6: The measurement principle diagram of the measurement module system with S parameter, 4 measurement antennas, and 4 ports FIG. 7: The measurement principle diagram of the measurement module system with S parameter, P (number) measurement antennas, and 2 ports FIG. 8: The measurement principle diagram of the measurement module system with S parameter, P (number) measurement antennas and V (number) ports FIG. 9: The detailed diagram of the 3-axis spherical scanner implementation FIG. 10: The detailed diagram of the 5-axis spherical scanner implementation FIG. 11: Positioning of the patient in the breast cancer imaging device with microwave surface impedance.

FIG. 12: The view showing angular movement of the lower axes of the 3-axis and 5-axis scanners during scanning.

DESCRIPTION OF REFERENCE NUMERALS

The parts in the figures are numbered and the numbers corresponding thereto are given below.
1) Imaging computer
2) Measurement module or device with S parameter
3) Measurement antennas and mechanical scanning unit
4) Bed
5) Motor control unit
6) Power source module
7) Axis motors
8) Mechanical scanning unit
9) Measurement antennas
10) Motor control software
11) Image algorithm software
12) Main axis
13) Axis 1
14) Axis 2
15) Axis M
16) Measurement antenna 1 of Axis 1
17) Measurement antenna 2 of Axis 1
18) Measurement antenna j of Axis 1
19) Measurement antenna 1 of Axis 2
20) Measurement antenna 2 of Axis 2
21) Measurement antenna k of Axis 2
22) Measurement antenna 1 of Axis M
23) Measurement antenna 2 of Axis M
24) Measurement antenna l of Axis M
25) Microwave cable
26) Axis 1 motor
27) Axis 2 motor
28) Axis M motor
29) Main axis motor
30) Measurement antenna 1
31) Measurement antenna 2
35) Measurement antenna 3
36) Measurement antenna 4
37) Measurement antenna 5
38) Measurement antenna P
39) Microwave switching module
41) Platform for moving the main axis
42) Semicircular spring for moving axis 1
43) Semicircular spring for moving axis 2
44) Breast
45) Semicircular spring for moving axis 3
46) Semicircular spring for moving axis 4
47) Camera
48) Measurement antenna connecting points
49) Patient
50) Measurement hole
51) The section where imaging computer and measurement module with S parameter are provided
52) The section where mechanical scanner is provided
53) Motor control unit and power source unit

DETAILED DESCRIPTION OF THE INVENTION

In this detailed description, the preferred embodiments of the breast cancer imaging device with microwave surface impedance according to the invention will be described in order for the subject matter to be better understood.

In this detailed description, in order to make the invention easier to be understood in the frame of the figures given, the names, common names, together with proper names, or in a way to include the components comprised thereby, are included under the title "description of reference numerals". For example: The measurement antennas and mechanical scanning unit (3) shown in FIG. 2 includes the measurement antennas (9) and mechanical scanning unit (8). The components given in FIG. 3 by the name measurement antennas (9) are the common (i.e. general) names given for the following; measurement antenna 1 of axis 1 (16), measurement antenna 2 of axis 1 (17), measurement antenna j of axis 1 (18), measurement antenna 1 of axis 2 (19), measurement antenna 2 of axis 2 (20), measurement antenna k of axis 2 (21), measurement antenna 1 of axis M (22), measurement antenna 2 of axis M (23), and measurement antenna l of axis M (24) Moreover, measurement antenna 1 (30), measurement antenna 2 (31), measurement antenna 3 (35), measurement antenna 4 (36), measurement antenna 5 (37), measurement antenna P (38) are the components given under the common name measurement antennas (9). Measurement antennas (9) scatter electromagnetic wave in the form of continuous wave. Axis motors (7), on the other hand, define axis 1 motor (26), axis 2 motor (27), and axis M motor (28).

The overall view of the breast cancer imaging device with microwave surface impedance is given in FIG. 1. The device consists of three main sections. These are, the section (51) where imaging computer and measurement module with S parameter are provided, the section (52) where the mechanical scanner is provided, and the section (53) where motor control unit and power source unit are provided. In this figure, the measurement hole (50) where the patient (49) positions her breast is seen on the bed (4).

The breast cancer imaging device with microwave surface impedance comprises the following as main parts; an imaging computer (1), a measurement module or device with S parameter (scattering parameter) (2), measurement antennas and a mechanical scanning unit (3), a bed (4) where the patient lies during measurement, a motor control unit (5) which controls the motors moving the measurement antennas and axes in the mechanical scanning unit (3), and a power source module (6) which meets energy need of the whole system.

Measurement antennas (9) and axis motors (7) allowing movement of the measurement axes are disposed inside the mechanical scanning unit (8) which is provided under the bed (4) of the breast cancer imaging device with microwave surface impedance. Axis motors (7) and main axis motor (29), which are electric motors, are automatically controlled by the motor control unit (5) and the motor control software (10) installed in the imaging computer (1). Scattering parameters of the breast (44) are measured by the measurement module or device with S parameter (2) by using the measurement antennas (9) attached in the axis 1 (13), axis 2 (14), axis M (15) and moved by the axis motors (7) disposed on the mechanical scanning unit (8). S parameters of the breast (44) having been measured are assessed by the image algorithm software (11) installed in the imaging computer (1), thereby obtaining Microwave Breast Tomography.

The image algorithm software (11) evaluates the S parameters of the breast (44) having been measured; estimates and analyzes surface impedance on the breast surface by means of measurement antenna or measurement antennas (9) through measuring the electric field formed due to scattering of the electromagnetic wave applied by measurement antennas (9) again by means of measurement antennas (9); detects tumors via tomographic methods; decides whether tumor-like structures observed in the breast are malign or benign by classifying dielectric parameters of tissues; and activates said measurement antennas (9) as receiver/transmitter in accordance with the desired algorithm via electronic ignition.

The mechanical scanning unit (8) may consist of several lower axes (13, 14, 15), besides a main axis (12). All of the lower axes, i.e. axis 1 (13), axis 2 (14), or axis M (15), are provided on the main axis (12); and when the main axis (12) is moved by the main axis motor (29), the lower axes (13, 14, 15) thereon move together, as well.

In FIG. 4, the principal diagram of a scanner made up of a main axis (12) and lower axes M (number) thereon is given. Measurement antenna j (number) (9) and the motor (26) moving the axis 1 are shown on the axis 1 (13). The measurement antenna 1 of axis 1 (16), measurement antenna 2 of axis 1 (17), and measurement antenna j of axis 1 (18) are connected to measurement module with S parameter (2) by using cables (25) directly, or through the microwave switching module (39) having inlets in P number and at least two cutlets.

Likewise, the measurement antenna 1 of axis 2 (19), measurement antenna 2 of axis 2 (20), and measurement antenna k of axis 2 (21) which are provided on the axis 2 (14), i.e. the lower axis no 2, are moved by the axis 2 motor (27). The measurement antenna k (number) on the axis 2 (14) is connected to measurement module with S parameter (2) by using microwave cables (25) directly, or through the microwave switching module (39) having inlets in P number and at least two outlets.

Similarly, the measurement antenna 1 of axis M (22), measurement antenna 2 of axis M (23), and measurement antenna l of axis M (24) which are provided on the axis M (15), i.e. the lower axis no M, are moved by the axis M motor (28). All measurement antennas l (number) on the axis M (15) are connected to measurement module with S parameter (2) by using microwave cables (25) directly, and through the microwave switching module (39) having inlets in P number and at least two outlets.

Microwave principle diagram of a breast cancer imaging device with microwave surface impedance on which two measurement antennas (16, 17) are used and which is provided with a two-port measurement module or device with S parameter (2) is given in FIG. 5. The measurement antenna 1 of axis 1 (16), which is used as the measurement antenna no 1, and the measurement antenna 2 of axis 1 (17), i.e. the measurement antenna no 2, are directly connected to the two-port measurement module or device with S parameter (2) via microwave cables.

Microwave principle diagram of a breast cancer imaging device with microwave surface impedance on which four measurement antennas (16, 17, 19, 20) are used and which is provided with a four-port measurement module or device with S parameter (4) is given in FIG. 6. The measurement antenna 1 of axis 1 (16), which is used as the measurement antenna no 1, the measurement antenna 2 of axis 1 (17), the measurement antenna 1 of axis 2 (19), which is used as the measurement antenna no 3, and measurement antenna 2 of axis 2 (20), which is used as the measurement antenna no 4 are directly connected to the four-port measurement module or device with S parameter (4) via microwave cables.

Microwave principle diagram of a breast cancer imaging device with microwave surface impedance on which four measurement antennas (30, 31, 35, 36) are used and which is provided with a four-port measurement module or device with S parameter (4) is given in FIG. 6. The measurement antenna 1 (30), measurement antenna 2 (31), measurement antenna 3 (35), and measurement antenna 4 (36) are directly connected to the four-port measurement module or device with S parameter (2) via microwave cables (25).

Microwave principle diagram of a breast cancer imaging device with microwave surface impedance on which measurement antennas P in number are used and which is provided with a two-port measurement module or device with S parameter (2) is given in FIG. 7. The measurement antenna P (38) including measurement antenna 1 (30), measurement antenna 2 (31), measurement antenna 3 (35), measurement antenna 4 (36), measurement antenna 5 (37), and measurement antenna in p number, is connected to the two-port measurement module with S parameter by means of P-inlet and two-outlet microwave switching module (39) via microwave cables (25).

Microwave principle diagram of a breast cancer imaging device with microwave surface impedance on which measurement antennas P in number are used and which is provided with a V-port measurement module or device with S parameter (2) is given in FIG. 8. The measurement antenna P (38) including measurement antenna 1 (30), measurement antenna 2 (31), measurement antenna 3 (35), measurement antenna 4 (36), measurement antenna 5 (37), and measurement antenna in p number, is connected to the V-port measurement module with S parameter (40) by means of P-inlet and V-outlet microwave switching module (40) via microwave cables (25).

In FIG. 9, mechanical illustration of a three-axis scanner formed of one main axis (12) and two lower axes is shown. When the platform (41) allowing the main axis (12) to move rotates, the two semicircular springs attached thereon, namely the semicircular spring (42) allowing the movement of the axis 1 and the semicircular spring (43) allowing the movement of the axis 2, rotate, as well. In the meantime, the breast which is being measured remains stable. The semicircular spring (42) allowing the movement of the axis 1 and the semicircular spring (43) allowing the movement of the axis 2 move independently. S parameters of the breast (44) are measured by engaging as many measurement antennas as desired in the measurement antenna connecting points (48) disposed on the semicircular spring (42) allowing the movement of the axis 1 and the semicircular spring (43) allowing the movement of the axis 2. The main axis motor (29) moving the main axis (12) and the axis motors (7) moving the lower axes are shown in FIG. 9.

Figure 10:
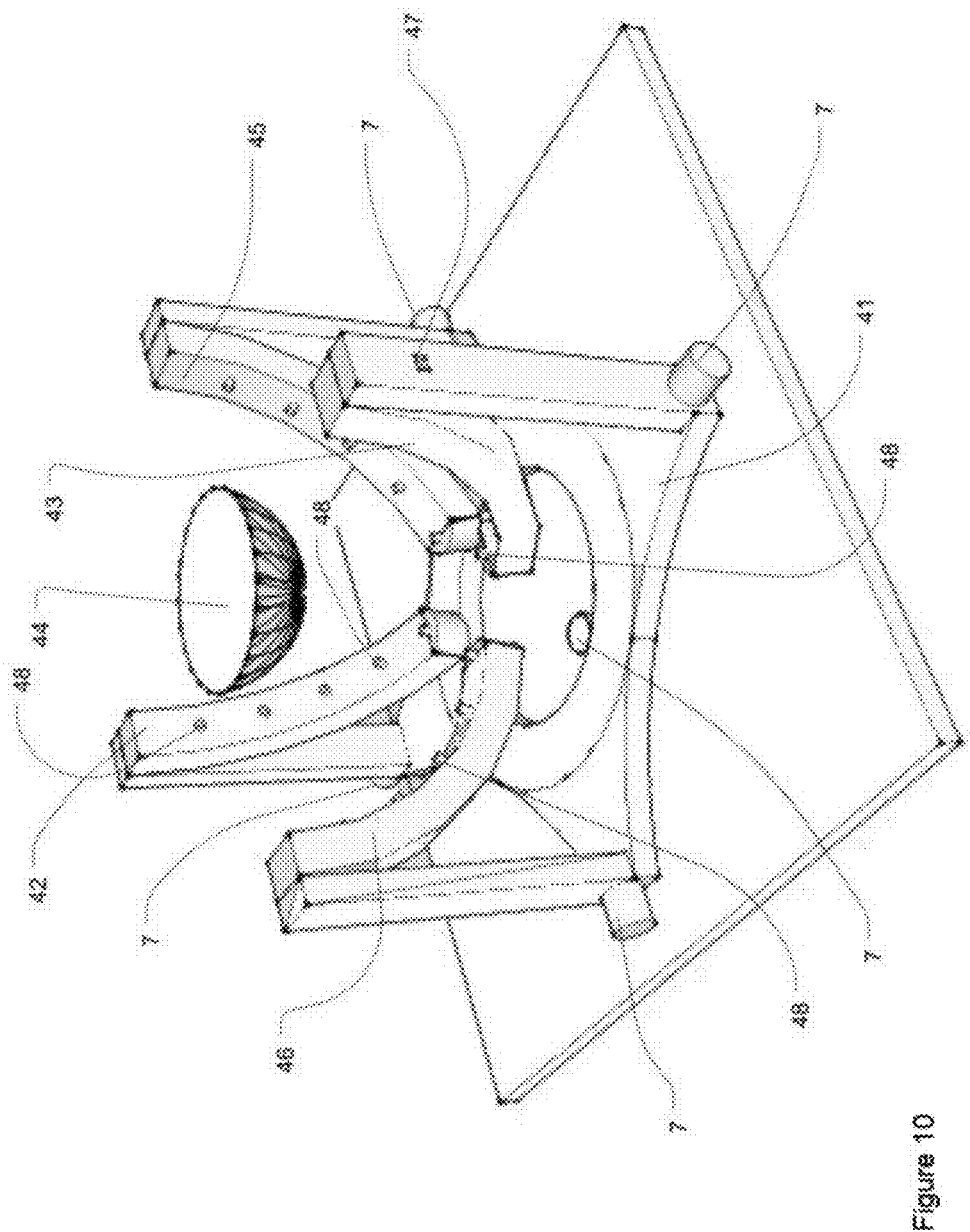

In FIG. 10, mechanical illustration of the five-axis implementation of the mechanical scanning unit (8) provided on the breast cancer imaging device or module with microwave surface impedance (2), is shown. Four semicircular springs on the platform (41) which allows the movement of the main axis as in FIG. 10, namely the semicircular spring (42) allowing the movement of the axis 1, the semicircular spring (43) allowing the movement of the axis 2, the semicircular spring (45) allowing the movement of axis 3, and the semicircular spring (46) allowing the movement of axis 4, move independent of one another. S parameters of the breast (44) are measured by engaging as many measurement antennas as desired in the measurement antenna connecting points (48) disposed on said semicircular springs (42, 43, 45, 46).

Figure 11:
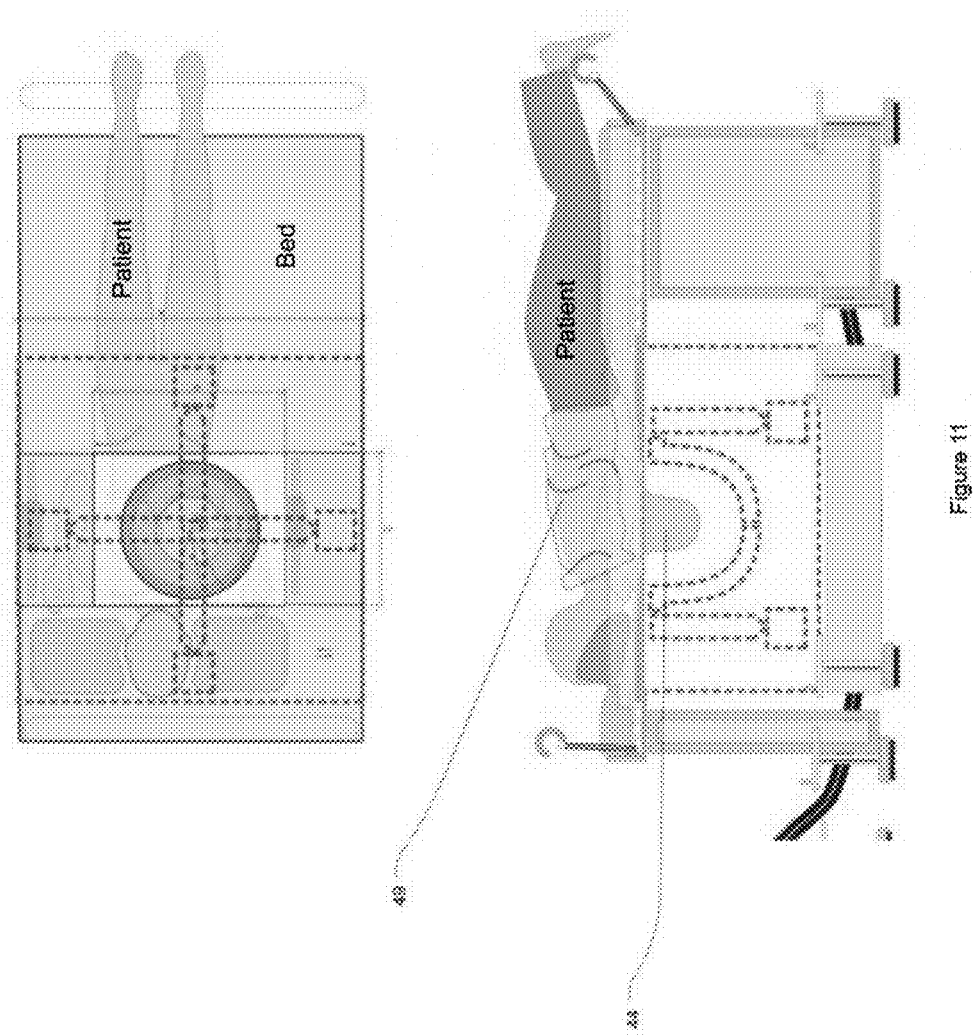

Positioning of the patient (49) in the breast cancer imaging device or module with microwave surface impedance (2) during measurement is shown in FIG. 11.

In order for the image algorithm to perform measurement accurately, 3-dimensional coordinates of the breast, the S parameters of which are to be measured, must be known. A camera (47) is used for measuring 3-dimensional coordinates of the breast (44). To that end, immediately before starting the tomography procedure, the semicircular spring (42, 43, 45, 46) assumes a position in a way not to get between the camera (47) and the breast (44), thereby making the platform (41) allowing the movement of the main axis rotate 360 degrees. While the platform (41) allowing the movement of the main axis rotates 360 degrees, the camera (47) takes peripheral image of the breast (44). Afterwards, the image algorithm software (11) Installed in the imaging computer (1) gets the contour of the breast (44) for every angle of the platform (41) allowing the movement of the main axis by using this video record and calculates linear coordinates of that contour. Then, these coordinates are combined and 3-dimensional coordinates of the outer surface of the breast (44) are obtained.

They are used for differentiation of the changes in the complex dielectric constants depending on the frequency, for the breast cancer imaging with microwave surface impedance using S parameters having been measured.

In FIG. 13 angular mobility of the lower axis semicircular springs of both three-axis and five-axis mechanical scanning unit (8) is shown. Attention must be paid to the fact that the semicircular springs (42, 43, 45, 46) on the platform (41) allowing the movement of the main axis are capable of performing angular movement independent of one another when said platform moves.

Recommended Model Formation Method to be Performed with the Device According to the Invention (MPM; Master Physiological Model)

Statistical results regarding the types, anatomy, physiological structure of the breast (44), and the changes in this structure depending on the age, weight, body type, menstruation, menopause, pregnancy, childbirth, and puerperium have been reported in detail in medical studies. Accordingly, standard physiological breast variations (which could be significant in terms of electromagnetic field) are defined.

After determining 3-dimensional coordinates of the breast (44) having been measured, the breast is matched with the most suitable type mentioned in the previous paragraph by evaluating the personal patient info and a primary breast model (PM) is obtained.

This procedure is performed individually for both breasts (44) of the patient. It is known in literature that the likelihood of tumors in both breasts (44) is less than 3%. The similarity of two breasts (44) in terms of physiological structure is more than 80%. The images of two breasts (44) are taken individually and physiological similarity criterion is detected by comparing low resolution scanning values. Electric field difference for both breasts (4) is calculated and difference % is expressed. If electric field similarity of right and left breasts (44) is more than 90%, the healthy breast (44) is used as the "healthy breast model" by obtaining symmetry thereof using symmetry axis. This model will be called MPM (Master Physiological Model). If electric field similarity of both breasts (44) is less than 80%, Secondary Model (SM) is used by fixing the supposedly healthy breast with Primary Model.

In electromagnetic field scanning, low resolution data (the measurement performed in fewer points) is used first and SM breast model is given the last form by contrast source method, i.e. becoming MPM.

If there is any MMT data belonging to the patient in database and if no tumor is observed as a result of this measurement, evaluation is made together with the info belonging to the former measurement (a form where the following info is included; date/hour, age, weight, body type, menstruation, menopause, pregnancy, childbirth, puerperium, etc.; as well as technical properties and serial number of the measurement device), and this data is used as the required MPM reference model.

In order to minimize measurement deviation and errors, one point (mark) is made in the middle lower section of both breasts (44) of the patient to serve as a reference point by means of a tattoo machine. Marking of this point increases measurement precision.

After MPM is formed, the field measurement performed on the breast (44) with MMT is subtracted from MPM reference model values and the tumor is detected by applying surface impedance method.

The more real-like the obtained model is and/or the more the number of measurement points is, the smaller the size of the tumor likely to be found and the less the error rate is.

In order to be able to detect the tumors in the breast (44), multi-frequency measurements are performed simultaneously. It has been defined in literature that the penetration depth of each measurement frequency in the tissue will be different. For example, when 3-frequency measurement is performed, the breast (44) can be thought as 3 layers. The measurement performed at maximum frequency includes more information belonging to the section close to the surface. In case a tumor is not observed in this layer, the field herein is subtracted from the area of the 2nd layer, which is measured at a lower frequency; thus, the data to be analyzed is simplified and the process is repeated as many times as the measurement frequency in this manner.

If the patient has an MR, this MR value is used first in SM, and then in MPM (master physiological model) formation by being fixed, and for reducing errors. When the tissues are stimulated by electromagnetic wave, they generate a scattered electric field associated with their electrical characteristics and this electric field data can be used for determining electrical characteristics of tissues. These electrical characteristics include relative dielectric permeability (or dielectric constant) ∈r [F/m], magnetic permeability μr [H/m], and conductivity σ [S/m] of the objects. While magnetic permeability cannot be used as a distinctive size for the tissues in human body, dielectric permeability and conductivity can be used for differentiation the tissues. Here, a method defined as follows is suggested, $$\epsilon_c(f) = \epsilon_r(f) + i\frac{\sigma(f)}{2\pi f \epsilon_o}\left[(\epsilon)_o \approx 8.854 \times \frac{10^{-12}F}{m}\right]$$

said method being for the use of complex dielectric permeability in differentiation of the tissues. This method, which we call as Microwave Breast Impedance Tomography (MBIT), is a new imaging method; wherein it will be used for analyzing the impedance difference between the healthy breast and breasts with cancerous tumors and for detecting tumors. Mathematical background of the method is as below:

When the patient lies down on the bed and her breast hangs down, the environment made of rib cage and air may be modeled like a two-part space within the system. Suppose that the sources and measurements are positioned on $\Gamma_k$ and $\Gamma_\partial$ surfaces respectively, k represents wave number of the environment, M represents the breast, and $\partial M$ represents breast surface. Using the impedance limit condition on the breast, the following can be written:

$$\frac{\partial u}{\partial n}(r) + \frac{ik}{\eta(r)} u(r) = 0, r \in \delta M$$

Here, $$\eta(r) = \frac{Z}{Z_0}$$

represents normalized surface impedance, Z and $Z_0$ represent surface impedance and environment (space or another material) impedance respectively, and u represents total electric field on breast surface.

The total field on breast surface can be represented as $u=u_g+u_o$, the field scattered from the breast as $u_g$, and the area in the two-part space formed of rib cage and air as $u_o$. $u_o$ can be calculated numerically using the dyadic Green functions of two-part space, and thus the field scattered only from the breast is obtained (see [1]). However, here, $u_g$, i.e. the field scattered from the breast, will be obtained on $\Gamma_\partial$. Monolayer potential technique is used for obtaining the field on the breast from this field. Monolayer potential is defined as $\varphi$.

$$(Ar_o\varphi)(s) = \int_{\partial M} G(s,r')\varphi(r')a'S(r'), s \in \Gamma_\partial \qquad (X)$$

Here, G(s, r') will again be dyadic Green function in 3-dimensional space. Obtaining $\varphi$ with monolayer potential from this equation is a badly represented problem in terms of Hadamard. In order to overcome this, different regularization techniques can be used (see [2, 3]). Here, we suggest using Tikhonov regularization, thus:

$$\varphi = (\alpha I + A'A)^{-1} A'u_g$$

$\alpha$ can be written as regularization parameter, and (*)' as adjoint operator. Afterwards, in order to calculate the total field on the breast, is chosen in (X) equation this time, and this field is calculated as $$u_{\partial M} = u_{o\partial M} + A_{\partial M}\varphi$$

Here, $u_{\partial M}$ is the total field on the breast, and $u_{o\partial M}$ is the field covering the breast.

After this stage, the field on the surface of a healthy breast, $u_{\widetilde{\partial M(right)}}$, is tried to be estimated using the statistical breast model obtained by various methods mentioned above. In order to calculate the derivative on breast surface, it is required to obtain the states of the total fields on this surface that are derived with respect to surface normality. In order to calculate derivatives of these fields, the following formula will be used [3]:

$$\frac{\partial u_{\partial M}}{\partial n}(r) = \frac{\partial u_{o\partial M}}{\partial n}(r) + \int_{\partial M} \frac{\partial G(r,r)}{\partial n}\varphi(r)dS(r) - \frac{\varphi(r)}{2}$$

After this stage, the surface impedances are calculated as follows:

$$Z_{\partial M} = -\frac{i\omega\mu_o u_{\partial M}}{\frac{\partial u_{\partial M}}{\partial n}} \text{ and } Z_{\widetilde{\partial M(w)}} = -\frac{i\omega\mu_o u_{\widetilde{\partial M(w)}}}{\frac{\partial u_{\widetilde{M(w)}}}{\partial n}}$$

The contribution only of the scattered field from the tumor on the surface impedance is calculated as follows:

$$u_t = A_t(Z_{\partial M} - Z_{\widetilde{\partial M(w)}})$$

Here, $A_t$ is a low-pass filter; wherein it is only used for relatively reinforcing more accurate measurements at the side where the source is.

At this stage, we only calculated the contribution of the tumor to the surface impedance. This contribution also has the information regarding tumor position; however, an additional process must be performed to reveal this position information. This stage of the method is as follows: The outer geometry of the breast is determined according to the image taken by the camera. A simulation model where a tumor having electrical characteristics obtained in light of former clinical trials is placed in a homogeneous structure having the same geometry as the breast to be analyzed, is formed. This simulation is repeated for different positions of the tumor and the contribution of the tumor to the surface impedance is calculated. In this case, we expect the results obtained from these two processes (the one with real breast and the one performed with homogeneous breast in the computer) to be similar when positioning is performed closest to the actual position of the tumor within homogeneous structures, if so:

$$\sigma_k = \left\langle \frac{Z_{\partial M}}{\|Z_{\partial M}\|} \Big| \frac{Z_{\partial M(hom_k)}}{\|Z_{\partial M(hom_k)}\|} \right\rangle, k = 1, 2 \ldots, M$$

we decide that the location of the tumor in homogeneous breast where cross correlation function is at maximum is also the location of the actual tumor.

In this method, good results are obtained when the selection of statistical breast models is performed properly. There are many ways for selecting these models that could be recommended. The most suitable one of those is the use of two breasts as basis of one another. However, it is also a fact that we can form statistical models from the data bank that we obtain as a result of the measurements.

In a preferred embodiment of the invention, the image algorithm software (11) forms the breast tomography image by using the electric field measurement that it performs by means of scattering parameters of electromagnetic waves in microwave frequency band in the form of continuous, i.e. not pulsed, non-ionizing waves with a power less than 100 mW.

In a preferred embodiment of the invention, the image algorithm software (11) forms the breast tomography image by measuring the scattering parameters of electromagnetic wave applied on the breast in many frequencies between bands 500 Mhz to 10 GHz at any measured point and by using the measurements in calculations.

REFERENCES

[1] Altuncu, Y., A. Yapar, and I. Akduman, "Numerical computation of the green's function of a layered media with rough interfaces," Microwave and Optical Technology Letters, Vol. 49, No. 5, 1204-1209, 2007. http: http://onlinelibrary.wiley.com/doi/10.1002/mop.22401/abstract

[2] Kirsch, A., An Introduction to the Mathematical Theory of Inverse Problems, Vol. 120, Springer, 2011. http://link.springer.com/book/10.1007%20978-1-4419-8474-6

[3] Akduman A., Kress R., "Direct and inverse scattering problems for inhomogeneous impedance cylinders of arbitrary shape", Radio Science 38, 1055-1064 (2003) http://www.agu.org/pubs/crossref/2003/2002RS002631.shtml

The invention claimed is:

1. A breast cancer imaging apparatus with microwave surface impedance, the breast cancer imaging apparatus comprising:
   an imaging computer;
   a bed having a measurement hole, said bed adapted to allow a patient to lie thereon during measurement;
   a mechanical scanning unit cooperative with said imaging computer and adapted to scan the patient;
   a power source module electrically connected to said imaging computer and said mechanical scanning unit so as to provide power thereto;
   a main axis having at least one axis;
   an axis motor driving connected to said main axis so as to move said main axis;
   a motor control software installed in a motor control unit and in said imaging computer, said motor control software controlling said axis motor;
   a measurement antenna adapted to scatter electromagnetic waves in a continuous wave form, said measurement antenna positioned on said main axis;
   a port measurement device cooperative with said measurement antenna so as to measure the scattered electromagnetic waves with a S parameter obtained by using the measurement antenna;
   a microwave cable connecting said measurement antenna to said port measurement device;
   a platform cooperative with said main access so as to move said main access;
   a semicircular spring connected to said main axis so as to move the at least one axis;
   a measurement antenna connecting point positioned on said semicircular spring;
   an optical camera directed towards said bed and adapted to measure three dimensional coordinates of the breast; and
   image algorithm software that assesses the S parameters, said image algorithm software installed in said imaging computer, said image algorithm software adapted to estimate and analyze the surface impedance on a surface of the breast by using the port measurement device to measure an electric field formed due to the scattered electromagnetic waves applied by the measurement antenna so as to determine whether tumeric structures in the breast are malignant or benign by classifying dielectric parameters, said image algorithm software activating said measurement antenna as either a transmitter or receiver via electronic ignition.

2. The breast cancer imaging apparatus of claim 1, further comprising:
   a microwave switching module having at least one inlet and at least two outlets, said microwave switching module connecting said measurement antenna to said port measurement device directly by the microwave cable or through the inlet and the outlets.

3. The breast cancer imaging apparatus of claim 1, said main axis comprising a first axis and a second axis, said first axis being a first moving arm, said second axis being a second moving arm, said first and second moving arms carrying the measurement cable and the measurement antenna.

4. The breast cancer imaging apparatus of claim 3, said axis motor comprising a first motor that moves said first arm and a second motor that moves said second arm.

5. The breast cancer imaging apparatus of claim 1, said axis motor comprising a main axis motor that moves said main axis.

6. The breast cancer imaging apparatus of claim 1, said measurement antenna comprising a first measurement antenna on a first axis and a second measurement antenna on a second axis.

7. The breast cancer imaging apparatus of claim 1, said semicircular spring comprising a first semicircular spring allowing a movement of a first axis, a second semicircular spring allowing a movement of a second axis, a third semicircular spring allowing a movement of a third axis, and a fourth semicircular spring allowing a movement of a fourth axis, the first axis and the second axis and the third axis and the fourth axis are respectively four moving arms that each carry said microwave cable to the measurement antenna so as to provide symmetrical scanning.

8. The breast cancer imaging apparatus of claim 1, said image algorithm software adapted to form a breast tomography image by using the electric field measurement in a microwave frequency band.

9. The breast cancer imaging apparatus of claim 1, said image algorithm software adapted to form a breast tomography image by measuring the scattering parameters of the electromagnetic waves applied to the breast in multiple frequencies between 500Mhz to 10 GHz at any measured point.

* * * * *